us008232356B2

(12) United States Patent
Leyrer et al.

(10) Patent No.: US 8,232,356 B2
(45) Date of Patent: Jul. 31, 2012

(54) METHOD FOR PRODUCING A THICKENER DISPERSION

(75) Inventors: Reinhold J. Leyrer, Dannstadt-Schauernheim (DE); Kati Schmidt, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 47 days.

(21) Appl. No.: 12/681,856

(22) PCT Filed: Nov. 13, 2008

(86) PCT No.: PCT/EP2008/065447
§ 371 (c)(1),
(2), (4) Date: Apr. 6, 2010

(87) PCT Pub. No.: WO2009/062994
PCT Pub. Date: May 22, 2009

(65) Prior Publication Data
US 2010/0210771 A1    Aug. 19, 2010

(30) Foreign Application Priority Data
Nov. 14, 2007    (EP) .................................... 07120725

(51) Int. Cl.
C08F 2/24 (2006.01)
(52) U.S. Cl. ................. 526/81; 526/79; 526/80; 526/86; 526/87
(58) Field of Classification Search .............. 526/79, 526/80, 81, 86, 87
See application file for complete search history.

(56) References Cited

U.S. PATENT DOCUMENTS

| | | | |
|---|---|---|---|
| 3,234,258 A | 2/1966 | Morris | |
| 3,557,039 A | 1/1971 | McIntyre et al. | |
| 3,887,806 A | 6/1975 | Rodak et al. | |
| 4,423,199 A | 12/1983 | Chang et al. | |
| 4,569,965 A | 2/1986 | Engel et al. | |
| 4,746,456 A | 5/1988 | Kud et al. | |
| 4,846,994 A | 7/1989 | Kud et al. | |
| 4,846,995 A | 7/1989 | Kud et al. | |
| 4,849,126 A | 7/1989 | Kud et al. | |
| 4,904,408 A | 2/1990 | Kud et al. | |
| 5,075,041 A | 12/1991 | Lutz | |
| 5,142,020 A | 8/1992 | Kud et al. | |
| 5,227,446 A | 7/1993 | Denzinger et al. | |
| 5,399,286 A | 3/1995 | Funhoff et al. | |
| 5,639,841 A | 6/1997 | Jenkins | |
| 6,268,065 B1 * | 7/2001 | Scheuermann et al. | 428/520 |
| 6,596,804 B1 * | 7/2003 | Edwards et al. | 524/458 |
| 6,887,933 B2 * | 5/2005 | Even | 524/556 |
| 2004/0143074 A1 * | 7/2004 | Throne et al. | 526/65 |

FOREIGN PATENT DOCUMENTS

| | | |
|---|---|---|
| DE | 37 11 299 | 10/1988 |
| DE | 41 06 355 | 9/1992 |
| DE | 43 13 909 | 11/1994 |
| DE | 44 15 623 | 11/1995 |
| EP | 0 001 004 | 3/1979 |
| EP | 0 013 836 | 8/1980 |
| EP | 0 185 427 | 6/1986 |
| EP | 0 241 984 | 10/1987 |
| EP | 0 241 985 | 10/1987 |
| EP | 0 272 033 | 6/1988 |
| EP | 0 396 303 | 11/1990 |
| EP | 0 451 508 | 10/1991 |
| EP | 0 454 126 | 10/1991 |
| EP | 0 511 037 | 10/1992 |
| EP | 0 581 452 | 2/1994 |
| EP | 0 656 914 | 6/1995 |
| EP | 0 658 579 | 6/1995 |
| EP | 0 729 989 | 9/1996 |
| FR | 1 156 513 | 5/1958 |
| GB | 839 407 | 6/1960 |
| GB | 873 214 | 7/1961 |
| GB | 1 154 730 | 6/1969 |
| JP | 58 217598 | 12/1983 |
| WO | 90 13533 | 11/1990 |
| WO | 92 16493 | 10/1992 |
| WO | 93 22362 | 11/1993 |
| WO | 94 01486 | 1/1994 |
| WO | 99 65958 | 12/1999 |
| WO | 2006 016035 | 2/2006 |

OTHER PUBLICATIONS

U.S. Appl. No. 12/671,596, filed Feb. 1, 2010, Leyrer, et al.

* cited by examiner

*Primary Examiner* — David W Wu
*Assistant Examiner* — Vu A Nguyen
(74) *Attorney, Agent, or Firm* — Oblon, Spivak, McClelland, Maier & Neustadt, L.L.P.

(57) ABSTRACT

A method is described for producing an aqueous thickener dispersion from a monomer composition made of at least one ethylenically unsaturated carboxylic acid and at least one ethylenically unsaturated hydrophobic monomer,
(i) an at least partially polymerized pre-emulsion being produced from 10 to 80 wt.-% of said monomer composition, and
(ii) the residual quantity of said monomer composition being added completely to the at least partially polymerized pre-emulsion and initiating a radical polymerization.
The monomer composition preferably also comprises an associative monomer. The method avoids disadvantages of batch polymerization, such as inadequate batch-to-batch reproducibility and safety problems.

16 Claims, No Drawings

METHOD FOR PRODUCING A THICKENER DISPERSION

CROSS-REFERENCE TO RELATED APPLICATIONS

This application is a 371 of PCT/EP08/065447 filed Nov. 13, 2008 and claims the benefit of EP 0720725.2 filed Nov. 14, 2007.

The invention relates to a method of preparing a thickener dispersion, i.e. an aqueous dispersion of an alkali-soluble copolymer which is suitable as thickener. The invention furthermore relates to the thickener dispersion obtainable in this way and to its use for modifying the rheology of paper sizes, textile printing pastes, medicaments, cosmetic compositions, detergents, cleaners or foods.

"Alkali-soluble" means that the addition of alkali to the dispersion leads to the dissolution or swelling of the dispersed copolymer particles and to a thickening and increase in viscosity. In order to achieve this thickening effect, the copolymers comprise copolymerized units of ethylenically unsaturated carboxylic acids alongside units of hydrophobic monomers.

A particular form of alkali-soluble thickeners are associative thickeners. The associative thickeners have hydrophobic or surfactant-like side groups. They are able, in a hydrophilic medium to interact both with themselves and also with other hydrophobic substances, such as surfactant micelles, pigments, binder particles or fillers, and to form noncovalent networks. The associative network resulting therefrom thickens or gels the medium.

EP-A 0 013 836 discloses emulsion copolymers which comprise (i) 20 to 69.5% by weight of (meth)acrylic acid, (ii) 0.5 to 25% by weight of a monomer of the formula $CH_2=C(R)-C(O)-O-(CH_2CH_2O)_n-R^o$, in which R is H or $CH_3$, n is at least 2 and $R^o$ is $C_8$-$C_{30}$-alkyl, and (iii) at least 30% by weight of a $C_1$-$C_4$-alkyl(meth)acrylate. Following neutralization with alkali, the copolymers serve as thickeners for coatings, detergents and the like.

WO 99/65958 describes alkali-soluble thickeners which comprise the reaction product of an unsaturated carboxylic acid, of a ethylenically monounsaturated monomer and of a hydrophobic, alkoxylated macromonomer. The ethylenically monounsaturated monomer comprises a methyl group; it is preferably methyl acrylate. These polymers reportedly become soluble even at pH 4.5 to 6.0 and are therefore suitable for cosmetic products.

WO 2006/016035 relates to the use of a water-soluble acrylic polymer as thickener in pigmented aqueous preparations. The acrylic polymer consists of an ethylenically unsaturated monomer with carboxyl function, an ethylenically unsaturated nonionic monomer and an ethylenically unsaturated oxyalkylated monomer which is terminated with a hydrophobic nonaromatic branched chain having 10 to 24 carbon atoms.

Typically, the thickener dispersions are prepared by a batch polymerization. The batch polymerization has the advantage that it produces high conversions and high molecular weights of the copolymers, which are desired for an optimum thickening effect. The disadvantage of the batch polymerization lies in the fact that the course of the polymerization is difficult to control, which may lead to unsatisfactory batch-to-batch reproducibility. In addition, the batch polymerization on an industrial scale also harbors safety problems since a large amount of polymerizable compounds, as is initially introduced in the case of the batch polymerization, may lead to explosive reactions in the case of an unforeseen course of the polymerization.

The object of the invention is to overcome the problems described above.

The object is achieved according to the invention by a method of preparing an aqueous thickener dispersion from a monomer composition which comprises:
a) at least one ethylenically unsaturated carboxylic acid, and
b) at least one ethylenically unsaturated hydrophobic monomer,
where
(i) an at least partially polymerized pre-emulsion is prepared from 10 to 80% by weight, preferably 40 to 70% by weight, of the monomer composition and
(ii) the remainder of the monomer composition is added in its entirety to the at least partially polymerized pre-emulsion and a free-radical polymerization is initiated.

In step (i), the at least partially polymerized pre-emulsion is usually prepared in the presence of a thermally activatable initiator or a redox initiator. The use of a thermally activatable initiator is preferred.

Suitable thermally activatable free-radical initiators are primarily those of the peroxy and azo types. These include, inter alia, hydrogen peroxide, peracetic acid, t-butyl hydroperoxide, di-t-butyl peroxide, dibenzoyl peroxide, benzoyl hydroperoxide, 2,4-dichlorobenzoyl peroxide, 2,5-dimethyl-2,5-bis(hydroperoxy)hexane, perbenzoic acid, t-butyl peroxypivalate, t-butyl peracetate, dilauroyl peroxide, dicapryloyl peroxide, distearoyl peroxide, dibenzoyl peroxide, diisopropyl peroxydicarbonate, didecyl peroxydicarbonate, dieicosyl peroxydicarbonate, di-t-butyl perbenzoates, azobisisobutyronitrile, 2,2'-azobis-2,4-dimethylvaleronitrile, ammonium persulfate, potassium persulfate, sodium persulfate and sodium perphosphate.

The use of thermally activable free-radical initiators whose unreacted fractions in step (i) can serve as oxidizing agent component of a redox initiator system for the initiation of the polymerization in step (ii) is expedient. The persulfates (peroxodisulfates), in particular sodium persulfate, are most preferred.

When carrying out the emulsion polymerization, the initiator is used in an adequate amount to initiate the polymerization reaction. The initiator is usually used in an amount of from about 0.01 to 3% by weight, based on the total weight of the monomers used. The amount of initiator is preferably about 0.05 to 2% by weight and in particular 0.1 to 1% by weight, based on the total weight of the monomers used.

The emulsion polymerization usually takes place at 35 to 140° C. It can be carried out either as a batch process or else in the form of a feed method. Preference is given to the monomer feed procedure in which at least some of the polymerization initiator and, if appropriate, some of the monomers are initially introduced and heated to the polymerization temperature and then the remainder of the polymerization mixture is introduced, usually via a plurality of separate feeds, continuously or stepwise to maintain the polymerization. Preferably, the monomer feed takes place in the form of a monomer emulsion. In parallel to the monomer feed, further polymerization initiator can be metered in.

In preferred embodiments, in step (i), the total initiator amount is initially introduced, i.e. no further initiator metered addition takes place in parallel to the monomer feed. It has surprisingly been found that this procedure leads to particularly high transparency and thickening performance of the thickener.

In a preferred embodiment, therefore, the thermally activatable free-radical polymerization initiator is initially introduced in its entirety, and the monomer mixture, preferably in the form of a monomer emulsion, is allowed to run in. Before starting the monomer mixture feed, the initial charge is brought to the activation temperature of the thermally activatable free-radical polymerization initiator or to a higher temperature. The activation temperature is considered to be the temperature at which half of the initiator is inactive after ten hours.

The degree of polymerization of the at least partially polymerized pre-emulsion obtained in this way is typically more than 80%, in particular more than 95%, particularly preferably more than 99%. The remainder of the monomer composition is then added in its entirety to the at least partially polymerized pre-emulsion, preferably in the form of a monomer emulsion, and a free-radical polymerization is initiated.

The polymerization can be initiated in various ways. For example, a thermally activatable free-radical initiator can be used, such as those specified above. Unconsumed thermally activatable initiator from step (i) may be sufficient or contribute to the initiation. When using a thermally activatable free-radical initiator, the initiation takes place, if appropriate, by heating to polymerization temperature.

In preferred embodiments, a redox initiator system is used for initiating the polymerization in step (ii).

A redox initiator system comprises at least one oxidizing agent component and at least one reducing agent component. Suitable oxidizing agent components are, for example, peroxides and/or hydroperoxides, such as hydrogen peroxide, tert-butyl peroxide, cumene hydroperoxide, pinan hydroperoxide, diisopropylphenyl hydroperoxide, dibenzoyl peroxide, dilauroyl peroxide and diacetyl peroxide. Hydrogen peroxide is preferred.

Suitable reducing agent components are, for example, cerium salts, manganese salts or iron(II) salts, alkali metal sulfites, ascorbic acid, acetone bisulfite adduct and/or an alkali metal salt of hydroxymethanesulfinic acid. A combination of iron(II) salts and ascorbic acid is preferred.

In a suitable embodiment, in step (ii), the free-radical polymerization is initiated by adding a reducing agent component of a redox initiator system. In this case, an oxidizing agent component of a redox initiator system has been added beforehand. Alternatively, excess initiator from step (i) can also act as an oxidizing agent component of a redox initiator system. The reducing agent component can be added in various ways. For example, the reducing agent component can be added all at once or as a continuous feed spread over a period of time.

In another suitable embodiment, in step (ii), the free-radical polymerization is initiated through essentially simultaneous addition of an oxidizing agent component of a redox initiator and of a reducing agent component of a redox initiator. The initiator and the components of the redox initiator system are used in an adequate amount to initiate the polymerization reaction.

It may be expedient, in step (ii), to leave the at least partially polymerized pre-emulsion to swell in the presence of the remainder of the monomer composition for at least one hour, e.g. 2 to 24 hours, before the free-radical polymerization is initiated.

In most cases, in step (ii), the remainder of the monomer composition will be added to the at least partially polymerized pre-emulsion within a period of time of less than one hour and, following complete addition, the free-radical polymerization will be initiated immediately.

The monomer composition comprises an adequate fraction of ethylenically unsaturated carboxylic acids for the resulting copolymer to be alkali-soluble. On the other hand, the monomer composition comprises an adequate fraction of ethylenically unsaturated hydrophobic monomers for the resulting copolymer to be essentially water-insoluble in the acidic and neutral pH range and to form a comparatively low viscosity dispersion. The copolymer dissolved in the alkaline range preferably forms a highly transparent solution in particular in the presence of surfactants, to which the hydrophobic constituents of the dissolved polymeric thickener impart a high compatibility. Preferably, the composition of the monomer mixture in step (i) and in step (ii) is identical. However, the compositions can also differ from one another by changing the concentrations of one or more monomers in steps (i) and (ii) relative to one another, or by using certain monomers only in one of the steps (i) or (ii). In any case, the monomer composition in step (i) and in step (ii) is in each case created such that both the pre-emulsion polymer and also the finished copolymer are alkali-soluble, but are insoluble in the acidic and neutral pH range.

The ethylenically unsaturated hydrophobic monomer is preferably selected from $C_1$-$C_9$-alkyl(meth)acrylates, dienes, vinyl aromatics, (meth)acrylonitrile and mixtures thereof.

The alkyl radical in the $C_1$-$C_9$-alkyl(meth)acrylates may be linear or branched. Suitable $C_1$-$C_9$-alkyl(meth)acrylates are, for example, methyl(meth)acrylate, ethyl(meth)acylate, n-propyl(meth)acrylate, n-butyl(meth)acrylate, ethylhexyl (meth)acrylate, nonyl(meth)acrylate, isononyl(meth)acrylate.

Suitable dienes are preferably conjugated $C_4$-$C_8$-dienes, such as, in particular, butadiene and isoprene.

Suitable vinyl aromatics are styrene and methylstyrenes.

In preferred embodiments, the ethylenically unsaturated hydrophobic monomer comprises:
b1) at least one $C_1$-$C_2$-alkyl methacrylate, and
b2) at least one $C_2$-$C_9$-alkyl acrylate, in particular $C_2$-$C_4$-alkyl acrylate, where the alkyl chain length averaged over the number of alkyl groups of the alkyl acrylate is at least 2.1.

The weight ratio b1):b2) is preferably 2:1 to 1:15.

Suitable $C_1$-$C_2$-alkyl methacrylates are methyl methacrylate and ethyl methacrylate, of which methyl methacrylate is particularly preferred.

Suitable $C_2$-$C_9$-alkyl acrylates are ethyl acrylate, n-propyl acrylate, n-butyl acrylate, ethylhexyl acrylate, nonyl acrylate and isononyl acrylate. The type and amount of the $C_2$-$C_4$-alkyl acrylates are chosen such that a certain alkyl chain length averaged over the number of alkyl groups of the $C_2$-$C_9$-alkyl acrylate units is established. Preferably, the averaged alkyl chain length is at least 2.1, in particular 2.1 to 4.0. The average alkyl chain length is calculated by multiplying the number of carbons in the longest alkyl chain of the alkyl radical (i.e. for example 2 for ethyl and 4 for n-butyl) by the molar fraction of the alkyl acrylate of the total amount of the $C_2$-$C_9$-alkyl acrylates, and adding the individual contributions.

Preferably, the $C_2$-$C_9$-alkyl acrylate comprises at least n-butyl acrylate, in particular a mixture of n-butyl acrylate with ethyl acrylate. Preferably, the copolymer comprises 5 to 85% by weight, based on the total weight of the copolymer, of copolymerized units of n-butyl acrylate, where a range from more than 10% by weight to 60% by weight is preferred and a range from 15% by weight to 45% by weight is particularly preferred.

In preferred embodiments, the monomer composition furthermore comprises at least one ethylenically unsaturated associative monomer. Associative monomers have hydrophobic or surfactant-like side groups which are able, in a hydrophilic medium, to interact both with themselves and also with other hydrophobic substances, such as surfactant micelles, pigments, binder particles or fillers, and to form noncovalent networks.

The ethylenically unsaturated associative monomer is selected, for example, from $C_{10}$-$C_{30}$-alkyl(meth)acrylates and ethylenically unsaturated surfactant monomers.

Nonionic ethylenically unsaturated surfactant monomers which are suitable as associative monomers are known per se. These are, for example,
(a) urethane-group-containing reaction products of a ethylenically monounsaturated isocyanate and nonionic surfactants
(b) esters of ethylenically unsaturated carboxylic acids and nonionic surfactants,
(c) allyl ethers of nonionic surfactants.

Suitable nonionic surfactants are preferably alkoxylated $C_6$-$C_{30}$-alcohols, such as fatty alcohol alkoxylates or oxo alcohol alkoxylates. At least 2, e.g. 2 to 100, preferably 3 to 20, mol of at least one $C_2$-$C_4$-alkylene oxide are used per mole of alcohol. Different alkylene oxide units can be arranged blockwise or can be present in random distribution. Ethylene oxide and/or propylene oxide are preferably used as alkylene oxide.

A further class of suitable nonionic surfactants is alkylphenol ethoxylates with $C_6$-$C_{14}$-alkyl chains and 5 to 30 mol of ethylene oxide units.

In preferred embodiments, the nonionic ethylenically unsaturated surfactant monomer has the general formula

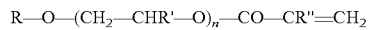

in which R is $C_6$-$C_{30}$-alkyl, preferably $C_8$-$C_{22}$-alkyl,
R' is hydrogen or methyl, preferably hydrogen,
R" is hydrogen or methyl, preferably methyl, and
n is an integer from 2 to 100, preferably 3 to 50.

The repeat units in the brackets are derived from ethylene oxide or propylene oxide. The meaning of R' is independent in each repeat unit from other repeat units. Different alkylene oxide units can be arranged blockwise or be present in random distribution.

The monomer composition can furthermore comprise an ethylenically polyunsaturated monomer. Ethylenically polyunsaturated monomers which can be used are, for example, ethylene glycol di(meth)acrylate, 1,6-hexanediol di(meth)acrylate, divinylbenzene and the like.

The ethylenically unsaturated carboxylic acid is generally a ethylenically monounsaturated mono- or dicarboxylic acid having 3 to 8 carbon atoms. Suitable ethylenically unsaturated carboxylic acids are selected, for example, from acrylic acid, methacrylic acid, itaconic acid and maleic acid. Of these, methacrylic acid is particularly preferred.

Typically, the monomer composition comprises:
a) 10 to 75% by weight, preferably 20 to 50% by weight, of ethylenically unsaturated carboxylic acid,
b) 5 to 90% by weight, preferably 15 to 80% by weight, of ethylenically unsaturated hydrophobic monomer,
c) 0 to 50% by weight, preferably 1 to 10% by weight, of ethylenically unsaturated associative monomer, and
d) 0 to 9% by weight of ethylenically polyunsaturated monomer.

The preparation of the at least partially polymerized preemulsion and/or the polymerization of the remainder of the monomer composition generally takes place in the presence of an anionic and/or nonionic emulsifier.

Typical emulsifiers are anionic emulsifiers, such as, for example, sodium lauryl sulfate, sodium tridecyl ether sulfates, dioctyl sulfosuccinate sodium salt and sodium salts of alkylaryl polyether sulfonates; and nonionic emulsifiers, such as, for example, alkylaryl polyether alcohols and ethylene oxide-propylene oxide copolymers.

Preferred emulsifiers have the general formula

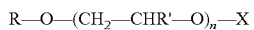

in which R is $C_6$-$C_{30}$-alkyl,
R' is hydrogen or methyl,
X is hydrogen or $SO_3M$,
M is hydrogen or an alkali metal, and
n is a number from 2 to 100.

The copolymer dispersion can be subjected to a chemical deodorization. In the chemical deodorization, when the actual emulsion polymerization is complete, a further initiator, e.g. a redox initiator, is added. Redox initiators suitable for the chemical deodorization comprise, as oxidizing component, for example at least one organic peroxide and/or hydroperoxide, such as hydrogen peroxide, tert-butyl peroxide, cumene hydroperoxide, pinane hydroperoxide, diisopropylphenyl hydroperoxide, dibenzoyl peroxide, dilauroyl peroxide and diacetyl peroxide, and, as reducing component, for example alkali metal sulfites, ascorbic acid, acetone bisulfite adduct and/or an alkali metal salt of hydroxymethanesulfinic acid, where iron(II) salts, preferably in complexed form, can be added as catalyst.

The copolymer dispersion generally has a solids content of from 25 to 70% by weight, in particular about 30 to 50% by weight.

In unneutralized form, the copolymer dispersion has a relatively low viscosity. It is therefore easy to handle and can be metered or circulated by pumping without problems. As a result of neutralization, e.g. to a pH of more than 5, preferably more than 6, in particular 8 to 10, the copolymer becomes soluble and the viscosity of the aqueous medium increases considerably. Here, preferably more than 50 mol % of the acid groups in the thickener are neutralized. Suitable neutralizing agents are, for example, sodium hydroxide, potassium hydroxide, ammonium hydroxide, amines, such as triethylamine, triethanolamine, monoethanolamine, and other alkaline materials.

The thickeners according to the invention are suitable for modifying the rheology of paper sizes, textile printing pastes, medicaments, cosmetic compositions, detergents, cleaners or foods. Particular preference is given to the use in liquid detergents and cleaners, in particular transparent liquid detergent or cleaner compositions.

Besides the thickener, the liquid detergents or cleaners comprise surfactant(s), where anionic, nonionic, cationic and/or amphoteric surfactants can be used. From an applications point of view, preference is given to mixtures of anionic and nonionic surfactants. The total surfactant content of the liquid detergents or cleaners is preferably 5 to 60% by weight and particularly preferably 15 to 40% by weight, based on the total liquid detergent or cleaner.

The nonionic surfactants used are preferably alkoxylated, advantageously ethoxylated, in particular primary alcohols having preferably 8 to 18 carbon atoms and on average 1 to 12 mol of ethylene oxide (EO) per mole of alcohol, in which the alcohol radical can be linear or preferably methyl-branched in the 2 position or can comprise linear and methyl-branched radicals in a mixture, as are usually present in oxo alcohol radicals. In particular, however, preference is given to alcohol ethoxylates with linear radicals from alcohols of native origin having 12 to 18 carbon atoms, for example from coconut alcohol, palm alcohol, tallow fatty alcohol or oleyl alcohol, and on average 2 to 8 EO per mole of alcohol. Preferred ethoxylated alcohols include, for example, $C_{12}$-$C_{14}$-alcohols with 3 EO, 4 EO or 7 EO, $C_9$-$C_{11}$-alcohol with 7 EO, $C_{13}$-

$C_{15}$-alcohols with 3 EO, 5 EO, 7 EO or 8 EO, $C_{12}$-$C_{18}$-alcohols with 3 EO, 5 EO or 7 EO and mixtures of these, such as mixtures of $C_{12}$-$C_{14}$-alcohol having 3 EO and $C_{12}$-$C_{18}$-alcohol having 7 EO. The stated degrees of ethoxylation are statistical average values which may be an integer or a fraction for a specific product. Preferred alcohol ethoxylates have a narrowed homolog distribution (narrow range ethoxylates, NRE). In addition to these nonionic surfactants, it is also possible to use fatty alcohols with more than 12 EO. Examples thereof are tallow fatty alcohols having 14 EO, 25 EO, 30 EO or 40 EO. It is also possible to use nonionic surfactants which comprise EO and PO groups together in the molecule. In this connection, it is possible to use block copolymers with EO-PO block units or PO-EO block units, but also EO-PO-EO copolymers or PO-EO-PO copolymers. It is of course also possible to use mixed alkoxylated nonionic surfactants in which EO and PO units are not in blockwise, but rather in random distribution. Such products are obtainable through the simultaneous action of ethylene oxide and propylene oxide on fatty alcohols.

Moreover, further nonionic surfactants that can be used are also alkyl glycosides of the general formula (1)

in which R is a primary straight-chain or methyl-branched, in particular 2-methyl-branched aliphatic radical having 8 to 22, preferably 12 to 18, carbon atoms, and G is a glycoside unit having 5 or 6 carbon atoms, preferably glucose. The degree of oligomerization x, which indicates the distribution of monoglycosides and oligoglycosides, is any desired number between 1 and 10; preferably, x is 1.2 to 1.4.

A further class of preferably used nonionic surfactants which are used either as the sole nonionic surfactant or in combination with other nonionic surfactants are alkoxylated, preferably ethoxylated or ethoxylated and propoxylated fatty acid alkyl esters, preferably having 1 to 4 carbon atoms in the alkyl chain, in particular fatty acid methyl esters, as are described, for example, in the Japanese patent application JP 58/217598 or which are preferably prepared by the method described in the international patent application WO-A-90/13533.

Nonionic surfactants of the amine oxide type, for example N-cocoalkyl-N,N-dimethyl-amine oxide and N-tallowalkyl-N,N-dihydroxyethylamine oxide, and of the fatty acid alkanolamide type may also be suitable. The amount of these nonionic surfactants is preferably not more than that of the ethoxylated fatty alcohols, in particular not more than half thereof.

Further suitable surfactants are polyhydroxy fatty acid amides of the formula (2),

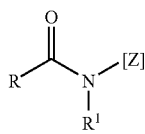

in which RC(=O) is an aliphatic acyl radical having 6 to 22 carbon atoms, $R^1$ is hydrogen, an alkyl or hydroxyalkyl radical having 1 to 4 carbon atoms and [Z] is a linear or branched polyhydroxyalkyl radical having 3 to 10 carbon atoms and 3 to 10 hydroxyl groups. The polyhydroxy fatty acid amides are known substances which can usually be obtained by reductive amination of a reducing sugar with ammonia, an alkylamine or an alkanolamine and subsequent acylation with a fatty acid, a fatty acid alkyl ester or a fatty acid chloride.

The group of polyhydroxy fatty acid amides also includes compounds of the formula (3)

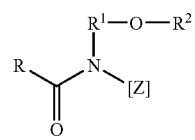

in which R is a linear or branched alkyl or alkenyl radical having 7 to 12 carbon atoms, $R^1$ is a linear, branched or cyclic alkylene radical having 2 to 8 carbon atoms or an arylene radical having 6 to 8 carbon atoms and $R^2$ is a linear, branched or cyclic alkyl radical or an aryl radical or an oxy-alkyl radical having 1 to 8 carbon atoms, where $C_1$-$C_4$-alkyl or phenyl radicals are preferred, and [Z] is a linear polyhydroxyalkyl radical whose alkyl chain is substituted by at least two hydroxyl groups, or alkoxylated, preferably ethoxylated or propoxylated derivatives of this radical. [Z] is preferably obtained by reductive amination of a sugar, for example glucose, fructose, maltose, lactose, galactose, mannose or xylose. The N-alkoxy- or N-aryloxy-substituted compounds can then be converted to the desired polyhydroxy fatty acid amides, for example in accordance with WO-A-95/07331, through reaction with fatty acid methyl esters in the presence of an alkoxide as catalyst.

The content of nonionic surfactants in the liquid detergents or cleaners is preferably 5 to 30% by weight, preferably 7 to 20% by weight and in particular 9 to 15% by weight, in each case based on the total composition.

The anionic surfactants used are, for example, those of the sulfonate and sulfate type. Suitable surfactants of the sulfonate type are preferably $C_9$-$C_{13}$-alkylbenzenesulfonates, olefinsulfonates, i.e. mixtures of alkene- and hydroxyalkane-sulfonates, and also disulfonates, as are obtained, for example, from $C_{12}$-$C_{18}$-monoolefins with terminal or internal double bond by sulfonation with gaseous sulfur trioxide and subsequent alkaline or acidic hydrolysis of the sulfonation products. Also suitable are alkane-sulfonates which are obtained from $C_{12}$-$C_{18}$-alkanes, for example by sulfochlorination or sulfoxidation with subsequent hydrolysis or neutralization. Likewise, the esters of α-sulfo fatty acids (ester sulfonates), for example the α-sulfonated methyl esters of the hydrogenated coconut, palm kernel or tallow fatty acids, are also suitable.

Further suitable anionic surfactants are sulfated fatty acid glycerol esters. Fatty acid glycerol esters are to be understood as meaning the mono-, di- and triesters, and mixtures thereof, as are obtained in the preparation by esterification of a monoglycerol with 1 to 3 mol of fatty acid or during the transesterification of triglycerides with 0.3 to 2 mol of glycerol. Preferred sulfated fatty acid glycerol esters here are the sulfation products of saturated fatty acids having 6 to 22 carbon atoms, for example of caproic acid, caprylic acid, capric acid, myristic acid, lauric acid, palmitic acid, stearic acid or behenic acid.

The alk(en)yl sulfates are preferably the alkali metal and in particular the sodium salts of the sulfuric acid half-esters of $C_{12}$-$C_{18}$-fatty alcohols, for example of coconut fatty alcohol, tallow fatty alcohol, lauryl alcohol, myristyl alcohol, cetyl alcohol or stearyl alcohol or of the $C_{10}$-$C_{20}$-oxo alcohols and those half-esters of secondary alcohols of these chain lengths.

Furthermore, preference is given to alk(en)yl sulfates of the specified chain length which comprise a synthetic, petrochemical-based straight-chain alkyl radical which have an analogous degradation behavior to the equivalent compounds based on fatty chemical raw materials. From a washing point of view, the $C_{12}$-$C_{16}$-alkyl sulfates and $C_{12}$-$C_{15}$-alkyl sulfates and also $C_{14}$-$C_{15}$-alkyl sulfates are preferred. 2,3-Alkyl sulfates, which are prepared, for example, in accordance with the U.S. Pat. No. 3,234,258 or 5,075,041 and can be obtained as commercial products from the Shell Oil Company under the name DAN®, are also suitable anionic surfactants.

The sulfuric acid monoesters of the straight-chain or branched $C_7$-$C_{21}$-alcohols ethoxylated with 1 to 6 mol of ethylene oxide, such as 2-methyl-branched $C_9$-$C_{11}$-alcohols with on average 3.5 mol of ethylene oxide (EO) or $C_{12}$-$C_{18}$-fatty alcohols with 1 to 4 EO, are also suitable. On account of their high foaming behavior, they are used in cleaners only in relatively small amounts, for example in amounts from 1 to 5% by weight.

Further suitable anionic surfactants are also the salts of alkylsulfosuccinic acid, which are also referred to as sulfosuccinates or as sulfosuccinic acid esters and which constitute monoesters and/or diesters of sulfosuccinic acid with alcohols, preferably fatty alcohols and in particular ethoxylated fatty alcohols. Preferred sulfosuccinates comprise $C_8$-$C_{18}$-fatty alcohol radicals or mixtures thereof. Particularly preferred sulfosuccinates comprise a fatty alcohol radical derived from ethoxylated fatty alcohols. In this connection, particular preference is in turn given to sulfosuccinates whose fatty alcohol radicals are derived from ethoxylated fatty alcohols with a narrow homolog distribution. It is likewise also possible to use alk(en)ylsuccinic acid having preferably 8 to 18 carbon atoms in the alk(en)yl chain or salts thereof.

Particularly preferred anionic surfactants are soaps. Saturated and unsaturated fatty acid soaps, such as the salts of lauric acid, myristic acid, palmitic acid, stearic acid, (hydrogenated) erucic acid and behenic acid, and also soap mixtures derived in particular from natural fatty acids, for example coconut, palm kernel, olive oil or tallow fatty acids, are suitable.

The anionic surfactants including the soaps can be present in the form of their sodium, potassium or ammonium salts, and also as soluble salts of organic bases, such as mono-, di- or triethanolamine. Preferably, the anionic surfactants are present in the form of their sodium or potassium salts, in particular in the form of the sodium salts.

The content of anionic surfactants in preferred liquid detergents or cleaners is 2 to 30% by weight, preferably 4 to 25% by weight and in particular 5 to 22% by weight, in each case based on the total composition. It is particularly preferred that the amount of fatty acid soap is at least 2% by weight and particularly preferably at least 4% by weight and particularly preferably at least 6% by weight.

The viscosity of the liquid detergents or cleaners can be measured by means of customary standard methods (for example Brookfield viscometer LVT-II at 20 rpm and 20° C., spindle 3) and is preferably in the range from 100 to 5000 mPas. Preferred compositions have viscosities of from 300 to 4000 mPas, with values between 1000 and 3000 mPas being particularly preferred.

In addition to the thickener and the surfactant(s), the liquid detergents or cleaners can comprise further ingredients which further improve the application and/or esthetic properties of the liquid detergent or cleaner. As a rule, in addition to the thickener and surfactant(s), preferred compositions comprise one or more substances from the group of builders, bleaches, bleach activators, enzymes, electrolytes, nonaqueous solvents, pH extenders, fragrances, perfume carriers, fluorescent agents, dyes, foam inhibitors, hydrotopes, silicone oils, antiredeposition agents, optical brighteners, graying inhibitors, antishrink agents, anticrease agents, color transfer inhibitors, antimicrobial active ingredients, germicides, fungicides, antioxidants, corrosion inhibitors, antistats, ironing aids, phobicization and impregnation agents, swelling and nonslip agents, and also UV absorbers.

Builders which may be present in the liquid detergents or cleaners are, in particular, silicates, aluminum silicates (in particular zeolites), and particularly preferably in the case of transparent liquid detergents, carbonates, salts of organic di- and polycarboxylic acids, and mixtures of these substances.

Suitable low molecular weight polycarboxylates as organic builders are, for example:

$C_4$-$C_{20}$-di-, -tri- and -tetracarboxylic acids, such as, for example, succinic acid, propanetricarboxylic acid, butanetetracarboxylic acid, cyclopentanetetracarboxylic acid and alkyl- and alkylenesuccinic acids with $C_2$-$C_{16}$-alkyl or -alkylene radicals;

$C_4$-$C_{20}$-hydroxycarboxylic acids, such as, for example, malic acid, tartaric acid, gluconic acid, glutaric acid, citric acid, lactobionic acid and sucrose mono-, di- and -tricarboxylic acid;

aminopolycarboxylates, such as, for example, nitrilotriacetic acid, methylglycinediacetic acid, alaninediacetic acid, ethylenediaminetetraacetic acid and serinediacetic acid;

salts of phosphonic acids, such as, for example, hydroxyethanediphosphonic acid, ethylenediamine tetra(methylenephosphonate) and diethylenetriamine penta(methylenephosphate).

Suitable oligomeric or polymeric polycarboxylates as organic builders are, for example:

oligomaleic acids, as are described, for example, in EP-A 0 451 508 and EP-A 0 396 303;

co- and terpolymers of unsaturated $C_4$-$C_8$-dicarboxylic acids, where ethylenically monounsaturated monomers
from group (i) in amounts of up to 95% by weight
from group (ii) in amounts of up to 60% by weight
from group (iii) in amounts of up to 20% by weight
may be present in copolymerized form as comonomers.

Suitable unsaturated $C_4$-$C_8$-dicarboxylic acids here are, for example, maleic acid, fumaric acid, itaconic acid and citraconic acid. Preference is given to maleic acid.

Group (i) comprises ethylenically monounsaturated $C_3$-$C_8$-monocarboxylic acids, such as, for example, acrylic acid, methacrylic acid, crotonic acid and vinylacetic acid. From group (i), preference is given to using acrylic acid and methacrylic acid.

Group (ii) comprises ethylenically monounsaturated $C_2$-$C_{22}$-olefins, vinyl alkyl ethers with $C_1$-$C_8$-alkyl groups, styrene, vinyl esters of $C_1$-$C_8$-carboxylic acid, (meth)acrylamide and vinylpyrrolidone. From group (ii), preference is given to using $C_2$-$C_6$-olefins, vinyl alkyl ethers with $C_1$-$C_4$-alkyl groups, vinyl acetate and vinyl propionate.

Group (iii) comprises (meth)acrylic esters of $C_1$-$C_8$-alcohols, (meth)acrylonitrile, (meth)acrylamides, (meth)acrylamides of $C_1$-$C_8$-amines, N-vinylformamide and vinylimidazole.

If the polymers of group (ii) comprise vinyl esters in copolymerized form, these may also be present in partially or completely hydrolyzed form to give vinyl alcohol structural units. Suitable co- and terpolymers are known, for example, from U.S. Pat. No. 3,887,806 and SE-A 43 13 909.

Copolymers of dicarboxylic acids suitable as organic builders are preferably:

copolymers of maleic acid and acrylic acid in the weight ratio 10:90 to 95:5, particularly preferably those in the weight ratio 30:70 to 90:10 with molar masses of from 10 000 to 150 000; terpolymers of maleic acid, acrylic acid and a vinyl ester of a $C_1$-$C_3$-carboxylic acid in the weight ratio 10 (maleic acid):90 (acrylic acid+vinyl ester) to 95 (maleic acid):10 (acrylic acid+vinyl ester), where the weight ratio of acrylic acid to vinyl ester can vary in the range from 20:80 to 80:20, and particularly preferably
terpolymers of maleic acid, acrylic acid and vinyl acetate or vinylpropionate in the weight ratio 20 (maleic acid):80 (acrylic acid+vinyl ester) to 90 (maleic acid):10 (acrylic acid+vinyl ester), where the weight ratio of acrylic acid to the vinyl ester can vary in the range from 30:70 to 70:30; copolymers of maleic acid with $C_2$-$C_8$-olefins in the molar ratio 40:60 to 80:20, where copolymers of maleic acid with ethylene, propylene or isobutane in the molar ratio 50:50 are particularly preferred.

Graft polymers of unsaturated carboxylic acids on low molecular weight carbohydrates or hydrogenated carbohydrates, cf. U.S. Pat. No. 5,227,446, DE-A 44 15 623, DE-A 43 13 909, are likewise suitable as organic builders.

Suitable unsaturated carboxylic acids here are, for example, maleic acid, fumaric acid, itaconic acid, citraconic acid, acrylic acid, methacrylic acid, crotonic acid and vinylacetic acid, and also mixtures of acrylic acid and maleic acid which are grafted on in amounts of from 40 to 95% by weight, based on the component to be grafted.

For the modification, additionally up to 30% by weight, based on the component to be grafted, of further ethylenically monounsaturated monomers may be present in copolymerized form. Suitable modifying monomers are the abovementioned monomers in groups (ii) and (iii).

Suitable graft bases are degraded polysaccharides, such as, for example, acidically or enzymatically degraded starches, inulins or cellulose, reduced (hydrogenated or reductively aminated) degraded polysaccharides, such as, for example, mannitol, sorbitol, aminosorbitol and glucamine, and also polyalkylene glycols with molar masses up to Mw=5000, such as, for example, polyethylene glycols, ethylene oxide/propylene oxide or ethylene oxide/butylene oxide block copolymers, random ethylene oxide/propylene oxide or ethylene oxide/butylene oxide copolymers, alkoxylated mono- or polybasic $C_1$-$C_{22}$-alcohols, cf. U.S. Pat. No. 4,746,456.

From this group, preference is given to using grafted degraded or degraded reduced starches and grafted polyethylene oxides, where 20 to 80% by weight of monomers, based on the graft component, are used in the graft polymerization. For the grafting, preference is given to using a mixture of maleic acid and acrylic acid in the weight ratio of from 90:10 to 10:90.

Polyglyoxylic acids as organic builders are described, for example, in EP-B 0 001 004, U.S. Pat. No. 5,399,286, DE-A 41 06 355 and EP-A 0 656 914. The end groups of the polyglyoxylic acids can have different structures.

Polyamidocarboxylic acids and modified polyamidocarboxylic acids as organic builders are known, for example, from EP-A 0 454 126, EP-B 0 511 037, WO-A 94/01486 and EP-A 0 581 452.

Preferably, the organic builders used are also polyaspartic acid or cocondensates of aspartic acid with further amino acids, $C_4$-$C_{25}$-mono- or -dicarboxylic acids and/or $C_4$-$C_{25}$-mono- or -diamines. Particular preference is given to using polyaspartic acids modified with $C_6$-$C_{22}$-mono- or -dicarboxylic acids or with $C_6$-$C_{22}$-mono- or -diamines and prepared in phosphorus-containing acids.

Condensation products of citric acid with hydroxycarboxylic acids or polyhydroxy compounds as organic builders are known, for example, from WO-A 93/22362 and WO-A 92/16493. Carboxyl-group-comprising condensates of this type usually have molar masses up to 10 000, preferably up to 5000.

Among the compounds which produce $H_2O_2$ in water and serve as bleaches, sodium perborate tetrahydrate and sodium perborate monohydrate have particular importance. Further bleaches that can be used are, for example, sodium percarbonate, peroxypyrophosphates, citrate perhydrates, and peracidic salts or peracids that produce $H_2O_2$, such as perbenzoates, peroxophthalates, diperazelaic acid, phthaloimino peracid or diperdodecanedioic acid.

In order to achieve an improved bleaching effect during washing at temperatures of 60° C. and below, bleach activators can be incorporated into the detergents or cleaners. Bleach activators which can be used are compounds which, under perhydrolysis conditions, produce aliphatic peroxocarboxylic acids having preferably 1 to 10 carbon atoms, in particular 2 to 4 carbon atoms, and/or optionally substituted perbenzoic acid. Substances which carry O- and/or N-acyl groups of the specified number of carbon atoms and/or optionally substituted benzoyl groups are suitable. Preference is given to polyacylated alkylenediamines, in particular tetraacetylethylenediamine (TAED), acylated triazine derivatives, in particular 1,5-diacetyl-2,4-dioxohexahydro-1,3,5-triazine (DADHT), acylated glycolurils, in particular tetraacetylglycoluril (TAGU), N-acylimides, in particular N-nonanoylsuccinimide (NOSI), acylated phenolsulfonates, in particular n-nonanoyl or isononanoyl oxybenzenesulfonate (n- or iso-NOBS), carboxylic acid anhydrides, in particular phthalic anhydride, acylated polyhydric alcohols, in particular triacetin, ethylene glycol diacetate and 2,5-diacetoxy-2,5-dihydrofuran.

In addition to the conventional bleach activators, or instead of them, it is also possible to incorporate so-called bleach catalysts into the liquid detergents or cleaners. These substances are bleach-boosting transition metal salts or transition metal complexes, such as, for example, Mn-, Fe-, Co-, Ru- or Mo-salene complexes or -carbonyl complexes. It is also possible to use Mn, Fe, Co, Ru, Mo, Ti, V and Cu complexes with nitrogen-containing tripod ligands, and also Co-, Fe-, Cu- and Ru-amine complexes as bleach catalysts.

Suitable enzymes are in particular those from the classes of the hydrolases, such as the proteases, esterases, lipases or lipolytic enzymes, amylases, cellulases and other glycosyl hydrolases and mixtures of said enzymes. All of these hydrolases contribute during washing to the removal of stains such as protein-, fat- or starch-containing stains and graying. Cellulases and other glycosyl hydrolases can moreover contribute to the color retention and to increasing the softness of the textile by removing pilling and microfibrils. Oxyreductases can also be used for the bleaching or for the inhibition of color transfer. Enzymatic active ingredients obtained from bacterial strains or fungi such as *Bacillus subtilis, Bacillus licheniformis, Streptomyceus griseus* and *Humicola insolens* are particularly well suited. Preference is given to using proteases of the subtilisin type and in particular proteases which are obtained from *Bacillus lentus*. Here, enzyme mixtures, for example of protease and amylase or protease and lipase or lipolytic enzymes or protease and cellulase or of cellulase and lipase or lipolytic enzymes or of protease, amylase and lipase or lipolytic enzymes or protease, lipase or lipolytic enzymes and cellulase, but in particular protease and/or lipase-containing mixtures or mixtures with lipolytic enzymes are of particular interest. Examples of such lipolytic enzymes are the known cutinases. Peroxidases or oxidases have also proven suitable in some cases. Suitable amylases include, in particular, α-amylases, isoamylases, pullulanases and pectinases. The cellulases used are preferably cellobiohydrolases, endoglucanases and β-glucosidases, which are also called cellobiases, or mixtures of these. Since different types of cellulase differ in their CMCase and avicelase activities, the desired activities can be established through targeted mixtures of the cellulases.

The enzymes can be adsorbed to carriers in order to protect them against premature decomposition. The fraction of the enzyme, enzyme mixtures or enzyme granules can be, for example, about 0.1 to 5% by weight, preferably 0.12 to about 2.5% by weight.

A broad number of highly diverse salts can be used as electrolytes from the group of inorganic salts. Preferred cations are the alkali and alkaline earth metals, preferred anions are the halides and sulfates. From the point of view of production, the use of NaCl or $MgCl_2$ in the compositions is preferred. The fraction of electrolytes in the compositions is usually 0.5 to 5% by weight.

Nonaqueous solvents which can be used in the liquid detergents or cleaners originate, for example, from the group of mono- or polyhydric alcohols, alkanolamines or glycol ethers, provided they are miscible with water in the stated concentration range. Preferably, the solvents are selected from ethanol, n- or isopropanol, butanols, glycol, propane- or butanediol, glycerol, diglycol, propyl or butyl diglycol, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl, ethyl or propyl ether, dipropylene glycol monomethyl or -ethyl ether, diisopropylene glycol monomethyl or -ethyl ether, methoxy-, ethoxy- or butoxytriglycol, isobutoxyethoxy-2-propanol, 3-methyl-3-methoxybutanol, propylene glycol t-butyl ether, and mixtures of these solvents. Nonaqueous solvents can be used in the liquid detergents or cleaners in amounts between 0.5 and 15% by weight, but preferably below 12% by weight and in particular below 9% by weight.

In order to bring the pH of the liquid detergents or cleaners into the desired range, the use of pH extenders may be appropriate. All known acids or alkalis can be used here, provided their use is not precluded for applications-related or ecological reasons or for reasons of consumer protection. Usually, the amount of these extenders does not exceed 7% by weight of the total formulation.

In order to improve the esthetic impression of the liquid detergents or cleaners, they can be colored with suitable dyes. Preferred dyes, the selection of which presents no difficulties at all to the person skilled in the art, have a high storage stability and insensitivity toward the other ingredients of the compositions and to light, and also no marked substantivity toward textile fibers, in order not to stain these.

Suitable foam inhibitors which can be used in the liquid detergents or cleaners are, for example, soaps, paraffins or silicone oils, which can if appropriate be applied to carrier materials.

Suitable antiredeposition agents, which are also referred to as soil repellents, are, for example, nonionic cellulose ethers, such as methylcellulose and methylhydroxypropyl-cellulose with a fraction of methoxy groups of from 15 to 30% by weight and of hydroxypropyl groups of from 1 to 15% by weight, in each case based on the nonionic cellulose ethers. Suitable soil release polymers are, for example, polyesters of polyethylene oxides with ethylene glycol and/or propylene glycol and aromatic dicarboxylic acids or aromatic and aliphatic dicarboxylic acids; polyesters of polyethylene oxides that are terminally capped at one end with di- and/or polyhydric alcohols and dicarboxylic acid, in particular polymers of ethylene terephthalates and/or polyethylene glycol terephthalates or anionically and/or nonionically modified derivatives of these. Of these, particular preference is given to the sulfonated derivatives of phthalic acid polymers and terephthalic acid polymers. Polyesters of this type are known, for example, from U.S. Pat. No. 3,557,039, GB-A 11 54 730, EP-A 0 185 427, EP-A 0 241 984, EP-A 0 241 985, EP-A 0 272 033 and U.S. Pat. No. 5,142,020. Further suitable soil release polymers are amphiphilic graft polymers or copolymers of vinyl and/or acrylic esters on polyalkylene oxides (cf. U.S. Pat. No. 4,746,456, U.S. Pat. No. 4,846,995, DE-A 37 11 299, U.S. Pat. No. 4,904,408, U.S. Pat. No. 4,846,994 and U.S. Pat. No. 4,849,126) or modified celluloses, such as, for example, methylcellulose, hydroxypropylcellulose or carboxymethyl-cellulose.

Optical brighteners (so-called whiteners) can be added to the liquid detergents or cleaners in order to eliminate graying and yellowing of the treated textile fabrics. These substances attach to the fibers and bring about a brightening and quasi-bleaching effect by converting invisible ultraviolet radiation into visible longer-wave light, where the ultraviolet light absorbed from the sunlight is emitted as pale bluish fluorescence and produces pure white with the yellow shade of grayed and/or yellowed laundry. Suitable compounds originate, for example, from the substance classes of the 4,4'-diamino-2,2'-stilbenedisulfonic acids (flavonic acids), 4,4'-distyrylbiphenylene, methylumbelliferones, coumarins, dihydroquinolinones, 1,3-diarylpyrazolines, naphthalimides, benzoxazole, benzisoxazole and benzimidazole systems, and the pyrene derivatives substituted by heterocycles. The optical brighteners are usually used in amounts between 0.03 and 0.3% by weight, based on the finished composition.

Graying inhibitors have the task of keeping the dirt detached from the fiber suspended in the liquor and thus preventing reattachment of the dirt. Of suitability for this purpose are water-soluble colloids mostly of an organic nature, for example glue, gelatin, salts of ether sulfonic acids of starch or of cellulose or salts of acidic sulfuric acid esters of cellulose or of starch. Water-soluble polyamides comprising acidic groups are also suitable for this purpose. Furthermore, soluble starch preparations and starch products other than those mentioned above can be used, for example degraded starch, aldehyde starches, etc. It is also possible to use polyvinylpyrrolidone. However, preference is given to using cellulose ethers, such as carboxymethylcellulose (Na salt), methylcellulose, hydroxyalkylcellulose and mixed ethers, such as methylhydroxy-ethylcellulose, methyl hydroxypropylcellulose, methylcarboxymethylcellulose and mixtures thereof in amounts of from 0.1 to 5% by weight, based on the compositions.

Since textile fabrics, in particular made of rayon, viscose rayon, cotton and mixtures thereof can have a tendency to crease because the individual fibers are sensitive to bending, folding, pressing and squeezing at right angles to the fiber direction, the compositions can comprise synthetic anticrease agents. These include, for example, synthetic products based on fatty acids, fatty acid esters, fatty acid amides, fatty alkylol esters, fatty alkylolamides or fatty alcohols, which are mostly reacted with ethylene oxide, or products based on lecithin or modified phosphoric acid esters.

To control microorganisms, the liquid detergents or cleaners can comprise antimicrobial active ingredients. A distinction is made here, depending on the antimicrobial spectrum and action mechanism, between bacteriostats and bactericides, fungistats and fungicides etc. Important substances from these groups are, for example, benzalkonium chlorides, alkylarylsulfonates, halophenols and phenol mercuriacetate.

In order to prevent undesired changes in the liquid detergents or cleaners and/or the treated textile fabrics caused by the effect of oxygen and other oxidative processes, the compositions can comprise antioxidants. This class of compound includes, for example, substituted phenols, hydroquinones, pyrocatechins and aromatic amines, and also organic sulfides, polysulfides, dithiocarbamates, phosphites and phosphonates.

Increased wear comfort can result from the additional use of antistats which are additionally added to the compositions. Antistats increase the surface conductivity and thus permit an improved discharging of charges formed. External antistats are generally substances with at least one hydrophilic molecule ligand and produce a more or less hygroscopic film on the surfaces. These mostly interface-active antistats can be divided into nitrogen-containing antistats (amines, amides, quaternary ammonium compounds), phosphorus-containing antistats (phosphoric acid esters) and sulfur-containing antistats (alkylsulfonates, alkyl sulfates). External antistats are described, for example, in the patent applications FR 1,156, 513, GB 873 214 and GB 839 407. The lauryl(or stearyl) dimethylbenzylammonium chlorides disclosed here are suitable as antistats for textile fabrics and as additive for detergents where a softening effect is additionally achieved.

To improve the water absorption capacity, the rewettability of the treated textile fabrics and to facilitate ironing of the treated textile fabrics, silicone derivatives, for example, can be used in the liquid detergents or cleaners. These additionally improve the wash-out behavior of the compositions through their foam-inhibiting properties. Preferred silicone derivatives are, for example, polydialkyl- or alkylarylsiloxanes in which the alkyl groups have one to five carbon atoms and are partially or completely fluorinated. Preferred silicones are polydimethylsiloxanes which can, if appropriate, be derivatized and then are aminofunctional or quaternized or have Si—OH, Si—H and/or Si—Cl bonds. The viscosities of the preferred silicones at 25° C. are in the range between 100 and 100 000 mPas, it being possible to use these silicones in amounts between 0.2 and 5% by weight, based on the total composition.

Finally, the liquid detergents or cleaners can also comprise UV absorbers which attach to the treated textile fabrics and improve the photostability of the fibers. Compounds which have these desired properties are, for example, the compounds and derivatives of benzophenone with substituents in the 2 and/or 4 position that are effective as a result of nonradiative deactivation. Furthermore, substituted benzotriazoles, acrylates phenyl-substituted in the 3 position (cinnamic acid derivatives), if appropriate with cyano groups in the 2 position, salicylates, organic Ni complexes, and natural substances such as umbelliferone and the endogenous urocanic acid are also suitable.

In order to avoid the decomposition of certain detergent ingredients catalyzed by heavy metals, it is possible to use substances which complex heavy metals. Suitable heavy metal complexing agents are, for example, the alkali metal salts of ethylenediaminetetraacetic acid (EDTA), of nitrilotriacetic acid (NTA) or methylglycinediacetic acid (MGDA), and also alkali metal salts of anionic polyelectrolytes such as polymaleates and polysulfonates.

A preferred class of complexing agents is the phosphonates, which are present in preferred liquid detergents or cleaners in amounts of from 0.01 to 2.5% by weight, preferably 0.02 to 2% by weight and in particular from 0.03 to 1.5% by weight. These preferred compounds include, in particular, organophosphonates, such as, for example, 1-hydroxyethane-1,1-diphosphonic acid (HEDP), aminotri(methylenephosphonic acid) (ATMP), diethylenetriaminepenta(methylenephosphonic acid) (DTPMP or DETPMP), and also 2-phosphonobutane-1,2,4-tricarboxylic acid (PBS-AM), which are mostly used in the form of their ammonium or alkali metal salts.

The resulting aqueous liquid detergents or cleaners have no sediment; in a preferred embodiment, they are transparent or at least translucent. Preferably, the aqueous liquid detergents or cleaners have a visible light transmission of at least 30%, preferably 50%, particularly preferably 75%, most preferably 90%. Alternatively, the thickeners according to the invention can be incorporated into opaque detergents or cleaners.

Besides these constituents, an aqueous detergent or cleaner can comprise dispersed particles, the diameter of which along their largest spatial expansion is 0.01 to 10 000 µm.

Particles may be microcapsules as well as granules, compounds and scented beads, with microcapsules being preferred.

The term "microcapsules" is understood as meaning aggregates which comprise at least one solid or liquid core which is surrounded by at least one continuous sheath, in particular a sheath made of polymer(s). Usually, these are finely dispersed liquid or solid phases surrounded by film-forming polymers, during the production of which the polymers, following emulsification and coacervation or interfacial polymerization, precipitate onto the material to be enveloped. The microscopically small capsules can be dried like powders. Besides single-core microcapsules, multicore aggregates are also known, also called microspheres, which comprise two or more cores in the continuous sheath material. Single-core or multicore microcapsules can additionally be surrounded by an additional second, third etc. sheath. Preference is given to single-core microcapsules with a continuous sheath. The sheath can consist of natural, semisynthetic or synthetic materials. Natural sheath materials are, for example, gum arabic, agar agar, agarose, maltodextrins, alginic acid and its salts, e.g. sodium alginate or calcium alginate, fats and fatty acids, cetyl alcohol, collagen, chitosan, lecithins, gelatin, albumin, shellac, polysaccharides, such as starch or dextran, sucrose and waxes. Semisynthetic sheath materials are, inter alia, chemically modified celluloses, in particular cellulose esters and ethers, e.g. cellulose acetate, ethyl-cellulose, hydroxypropylcellulose, hydroxypropylmethylcellulose and carboxymethylcellulose, and also starch derivatives, in particular starch ethers and esters. Synthetic sheath materials are, for example, polymers, such as polyacrylates, polyamides, polyvinyl alcohol or polyvinylpyrrolidone. In the interior of the microcapsules, sensitive, chemically or physically incompatible as well as volatile components (=active ingredients) of the aqueous liquid detergent or cleaner can be enclosed in a storage-stable and transport-stable manner. For example, optical brighteners, surfactants, complexing agents, bleaches, bleach activators, dyes and fragrances, antioxidants, builders, enzymes, enzyme stabilizers, antimicrobial active ingredients, graying inhibitors, antiredeposition agents, pH extenders, electrolytes, foam inhibitors and UV absorbers may be present in the microcapsules.

The microcapsules can also comprise cationic surfactants, vitamins, proteins, preservatives, detergency boosters or pearlizing agents. The fillings of the microcapsules can be solids or liquids in the form of solutions or emulsions or suspensions.

The microcapsules can have any desired form within the scope of manufacture, but are preferably approximately spherical. Their diameter along their largest spatial expansion can be between 0.01 μm (not visually recognizable as capsules) and 10 000 μm depending on the components present in their interior and the application. Preference is given to visible microcapsules with a diameter in the range from 100 μm to 7000 μm, in particular from 400 μm to 5000 μm. The microcapsules are accessible by known methods, with coacervation and interfacial polymerization being attributed the greatest importance. Microcapsules which can be used are all of the surfactant-stable microcapsules available on the market, for example the commercial products (the coating material is given in each in brackets) Hallcrest Microcapsules (gelatin, gum arabic), Coletica Thalaspheres (maritime collagen), Lipotec Millicapsules (alginic acid, agar agar), Induchem Unispheres (lactose, microcrystalline cellulose, hydroxypropylmethylcellulose); Unicerin C30 (lactose, microcrystalline cellulose, hydroxypropylmethylcellulose), Kobo Glycospheres (modified starch, fatty acid esters, phospholipids), Softspheres (modified agar agar) and Kuhs Probiol Nanospheres (phospholipids).

Alternatively, it is also possible to use particles which do not have a core-sheath structure, but in which the active ingredient is distributed in a matrix of a matrix-forming material. Such particles are also referred to as "speckies".

A preferred matrix-forming material is alginate. To produce alginate-based speckies, an aqueous alginate solution, which also comprises the active ingredient to be enclosed or the active ingredients to be enclosed, is dripped and then hardened in a precipitating bath comprising $Ca^{2+}$ ions or $Al^{3+}$ ions.

Alternatively, instead of alginate, other matrix-forming materials can be used. Examples of matrix-forming materials comprise polyethylene glycol, polyvinylpyrrolidone, polymethacrylate, polylysine, poloxamer, polyvinyl alcohol, polyacrylic acid, polyethylene oxide, polyethoxyoxazoline, albumin, gelatin, acacia, chitosan, cellulose, dextran, Ficoll®, starch, hydroxyethylcellulose, hydroxypropylcellulose, hydroxypropylmethylcellulose, hyaluronic acid, carboxymethylcellulose, carboxymethyl-cellulose, deacetylated chitosan, dextran sulfate and derivatives of these materials. The matrix formation takes place for these materials for example via gelling, polyanion-polycation interactions or polyelectrolyte-metal ion interactions. The preparation of particles with these matrix-forming materials is known per se.

The particles can be stably dispersed in the aqueous liquid detergents or cleaners. Stable means that the compositions are stable at room temperature and at 40° C. over a period of at least 4 weeks and preferably of at least 6 weeks without the composition creaming up or sedimenting. The thickeners according to the invention bring about, through the increase in viscosity, a kinetic slowing of the sedimentation of the particles and thus their stabilization in the suspended state.

The release of the active ingredients from the microcapsules or speckies usually takes place during the application of the compositions comprising them through decomposition of the sheath or of the matrix as a result of mechanical, thermal, chemical or enzymatic action.

The detergents or cleaners according to the invention can be used for the cleaning of textile fabrics and/or hard surfaces. Cleaners according to the invention can be in the form of a hand or machine dishwashing detergent, all-purpose cleaner for nontextile surfaces, e.g. made of metal, painted wood or plastic, or cleaner for ceramic products, such as porcelain, tiles. The detergents or cleaners may be formulated as liquids or pastes.

To prepare the liquid detergents or cleaners, the surfactants, the thickener and the optional components can be combined with one another in any desired order. For example, the acidic components, such as, for example, the linear alkylsulfonates, citric acid, boric acid, phosphonic acid, the fatty alcohol ether sulfates, etc. can be initially introduced, and the nonionic surfactants added thereto. Then, a base, such as, for example, NaOH, KOH, triethanolamine or monoethanolamine, followed by the fatty acid, if present, is added. Subsequently, the remaining ingredients and the solvents of the aqueous liquid detergent or cleaner are added to the mixture. Then, the thickener according to the invention is added and, if appropriate, the pH is corrected, e.g. to a value of from 8 to 9.5.

If appropriate, finally, particles to be dispersed can be added and, through mixing, homogeneously dispersed in the aqueous liquid detergent or cleaner.

The invention is illustrated in more detail by the examples below.

COMPARATIVE EXAMPLE 1

Preparation of a Thickener in the Single-Stage Emulsion Polymerization Process

In a stirred apparatus consisting of a 4 liter HWS vessel with anchor stirrer (150 rpm), reflux condenser, internal thermosensor and metering station, 478.73 g of demineralized water (dem. water) and 10.71 g of emulsifier Texapon NSO (sodium lauryl ether sulfate; 28% strength in water) were mixed as the initial charge.

At 75° C., 16.29 g of a 7% strength aqueous sodium peroxodisulfate solution were added to this solution and the mixture was stirred at 75° C. for 5 minutes. Then, at 75° C. and with further stirring, the emulsion consisting of 714 g of completely demineralized water (dem. water), the monomers (183.67 g of methacrylic acid and 420 g of ethyl acrylate) and the emulsifier (21.43 g of Texapon NSO 28% strength in water) was uniformly metered in over the course of 2 hours. Then, the reaction mixture was stirred for a further 1 hour at 75° C. and then brought to room temperature. At room temperature, 0.3 g of 4% strength Dissolvine® E-FE-6 solution (iron II salt solution) and 12 g of a 5% strength hydrogen peroxide solution were added, and 90 g of a 1% strength ascorbic acid solution were uniformly metered in over the course of 30 minutes.

COMPARATIVE EXAMPLE 2

Preparation of an Associative Thickener in the Single-Stage Emulsion Polymerization Process In a stirred apparatus consisting of a 4 liter HWS vessel with anchor stirrer (150 rpm), reflux condenser, internal thermosensor and metering station, 736.73 g of demineralized water (dem. water) and 10.71 g of emulsifier Texapon NSO (28% strength in water) were mixed as the initial charge.

At 75° C., 4.23 g of a 7% strength aqueous sodium peroxodisulfate solution were added to this solution and the mixture was stirred at 75° C. for 5 minutes. Then, at 75° C. and with further stirring, an emulsion consisting of 457.04 g of completely demineralized water (dem. water), the monomers (183.67 g of methacrylic acid and 360 g of ethyl acrylate, 15 g of Lutensol® AT 25 methacrylate [=$(C_{16-18})$-$(EO)_{25}$ methacrylate], 45 g of methyl methacrylate), and 10.71 g of emulsifier Texapon NSO 28% strength in water were uniformly metered in over the course of 2 hours, and at the same time, 12.06 g of 7% strength aqueous sodium peroxodisulfate solution were uniformly metered in over the course of 2 hours. Then, the reaction mixture was stirred for a further 1 hour at 75° C. and then brought to room temperature. At room temperature, 0.3 g of a 4% strength Dissolvine® E-FE-6 solution (iron II salt solution) and 12 g of a 5% strength hydrogen peroxide solution were added, and 90 g of a 1% strength ascorbic acid solution were uniformly metered in over the course of 30 minutes.

COMPARATIVE EXAMPLE 3

Preparation of an Associative Thickener in the Single-Stage Emulsion Polymerization Process In a stirred apparatus consisting of a 4 liter HWS vessel with anchor stirrer (150 rpm), reflux condenser, internal thermosensor and metering station, 736.73 g of demineralized water (dem. water) and 10.71 g of emulsifier Texapon NSO 28% strength in water were mixed as the initial charge.

At 75° C., 4.23 g of a 7% strength aqueous sodium peroxodisulfate solution were added to this solution and the mixture was stirred at 75° C. for 5 minutes. Then, at 75° C. and with further stirring, the emulsion consisting of 457.04 g of completely demineralized water (dem. water), the monomers (183.67 g of methacrylic acid and 300 g of ethyl acrylate, 60 g of n-butyl acrylate, 15 g of Lutensol® AT 25 methacrylate [=($C_{16-18}$)-$(EO)_{25}$ methacrylate], 45 g of methyl methacrylate), 10.71 g of emulsifier Texapon NSO 28% strength in water were uniformly metered in over 2 hours, and at the same time 12.06 g of 7% strength aqueous sodium peroxodisulfate solution were uniformly metered in over 2 hours (combine emulsion and sodium peroxodisulfate feed). Then, the reaction mixture was stirred for a further 1 hour at 75° C. and then brought to room temperature. At room temperature, 0.3 g of a 4% strength Dissolvine® E-FE-6 solution (iron II salt solution) and 12 g of a 5% strength hydrogen peroxide solution were added, and 90 g of a 1% strength ascorbic acid solution were uniformly metered in over 30 minutes.

EXAMPLE 1

Preparation According to the Invention of the Associative Thickener Dispersion Using Redox/Part Batch Procedure In a stirred apparatus consisting of a 2 liter HWS vessel with anchor stirrer (175 rpm), reflux condenser, internal thermosensor and metering station, 540.17 g of demineralized water (dem. water) and 8.21 g of emulsifier Texapon NSO 28% strength in water were mixed as the initial charge.

At 75° C., 12.49 g of a 7% strength aqueous sodium peroxodisulfate solution were added to this solution and the mixture was stirred at 75° C. for 5 minutes. Then, at 75° C. and with further stirring, 50% of the emulsion consisting of 429.91 g of completely demineralized water (dem. water), the monomers (140.82 g of methacrylic acid, 138.0 g of ethyl acrylate, 138.0 g of n-butyl acrylate, 11.5 g of Lutensol® AT 25 methacrylate [=($C_{16-18}$)-$(EO)_{25}$ methacrylate], 34.5 g of methyl methacrylate), and 16.73 g of emulsifier Texapon NSO 28% strength in water were metered in over 1 hour. Then, the reaction mixture was stirred for a further 1 hour at 75° C. When polymerization was complete, the remainder (50%) of the emulsion was added and the mixture was after stirred for 1 hour at 60° C. 0.23 g of a 4% strength Dissolvine® E-FE-6 solution (iron II salt solution) and 9.2 g of a 5% strength hydrogen peroxide solution were then added. 11.5 g of a 1% strength ascorbic acid solution were uniformly metered in over 2 hours. The mixture is then cooled to room temperature.

The other dispersions according to the invention, Example 2 to Example 21, listed in Table 1b to 1d below, were prepared analogously. The quantitative data for the feed materials are given in parts per 100 reactive monomer parts (parts per hundred monomers; pphm). In characterizing the dispersion, the following values were measured:

Solids content: the dispersion was dried for 30 min at 140° C. and the solids content was determined as a percentage from the ratio of dry residue to initial weight.

Particle size: the dispersion was diluted to 0.01% and the particle size was measured by means of light scattering in the High Performance Particle Sizer 5001 (HPPS) from Malvern Instruments.

LT value: the dispersion was diluted to 0.01% and the light transmission (LT) of the dispersion was measured optically in the Hach DR/2010 compared to pure water as a measure of the particle size.

PLEX® 6877-O in MMA methacrylic acid ester of an ethoxylated (25 mol EO) $C_{16}$-$C_{18}$-fatty alcohol mixture 25% strength in methyl methacrylate NaPS sodium peroxidisulfate n.d. not determined TABLE 1a

| Thickener dispersion | Comparison 1 | Comparison 2 | Comparison 3 |
|---|---|---|---|
| n-Butyl acrylate (pphm) | — | — | 10 |
| Ethyl acrylate (pphm) | 70 | 60 | 50 |
| Methacrylic acid (pphm) | 30 | 30 | 30 |
| PLEX ® 6877-O 25% strength in MMA (pphm) | — | 10 | 10 |
| Texapon NSO initial feed/E feed (pphm) | 0.5/1 | 0.5/0.5 | 0.5/0.5 |
| NaPS in initial charge (pphm) | 0.19 | 0.05 | 0.05 |
| NaPS - feed (pphm) | — | 0.14 | 0.14 |
| Polymerization temp. (° C.) | 75 | 75 | 75 |
| Solids content (%) | 30.5 | 30.2 | 30.4 |
| Particle size (nm) | 74 | 66 | 62 |
| LT - 0.01% strength (%) | 97 | 98 | 98 |

TABLE 1b

Thickener dispersions prepared according to the invention, polymerized with swelling

| Thickener dispersion | Example 1 | Example 2 | Example 3 | Example 4 | Example 5 | Example 6 | Example 7 |
|---|---|---|---|---|---|---|---|
| n-Butyl acrylate (pphm) | 30 | 30 | 30 | 30 | 30 | 30 | 30 |
| Ethyl acrylate (pphm) | 30 | 30 | 30 | 30 | 30 | 30 | 30 |
| Methacrylic acid (pphm) | 30 | 30 | 30 | 30 | 30 | 30 | 30 |
| PLEX 6877-O 25% strength in MMA (pphm) | 10 | 10 | 10 | 10 | 10 | 10 | 10 |
| Texapon NSO initial charge/E feed (pphm) | 0.5/1 | 0.5/1 | 0.5/1 | 0.5/1 | 0.5/1 | 0.5/1 | 0.5/1 |

TABLE 1b-continued

Thickener dispersions prepared according to the invention, polymerized with swelling

| Thickener dispersion | Example 1 | Example 2 | Example 3 | Example 4 | Example 5 | Example 6 | Example 7 |
|---|---|---|---|---|---|---|---|
| NaPS in initial charge (pphm) | 0.19 | 0.19 | 0.19 | 0.19 | 0.19 | 0.19 | 0.19 |
| NaPS - feed (pphm) | — | — | — | — | — | — | — |
| NaPS addition (pphm) | — | — | — | — | — | — | — |
| Hydrogen peroxide addition (pphm) | 0.1 | 0.1 | 0.1 | 0.1 | 0.1 | 0.1 | 0.1 |
| Ascorbic acid (pphm) | 0.025 | 0.015 | 0.15 | 0.15 | 0.15 | 0.15 | 0.1 |
| Polymerization temp. (° C.) | 75 | 75 | 75 | 75 | 75 | 75 | 75 |
| Addition of the remaining monomer emulsion (min) | 60 | 5 | 5 | 5 | 5 | 5 | 5 |
| Swelling (min) | 60 | about 55 | about 45 | about 35 | about 30 | about 25 | about 45 |
| Part batch exit temp. (° C.) | 60 | 23 | 30 | 40 | 50 | 60 | 30 |
| Solids content (%) | 30.6 | 30.6 | 30.5 | 30.3 | 30.5 | 30.7 | 30.6 |
| Particle size (nm) | 62 | 64 | 64 | 66 | 64 | 64 | 63 |
| LT - 0.01% strength (%) | 98 | 98 | 98 | 98 | 98 | 98 | 98 |

TABLE 1c

Thickener dispersions prepared according to the invention, polymerized with swelling

| Thickener dispersion | Example 8 | Example 9 | Example 10 | Example 11 | Example 12 | Example 13 | Example 14 |
|---|---|---|---|---|---|---|---|
| n-Butyl acrylate (pphm) | 30 | 30 | 30 | 30 | | 60 | 35 |
| Ethyl acrylate (pphm) | 30 | 30 | 30 | 30 | 60 | | 35 |
| Methacrylic acid (pphm) | 30 | 30 | 30 | 30 | 30 | 30 | 30 |
| Acrylic acid (pphm) | — | — | — | — | — | — | — |
| PLEX 6877-O 25% strength in MMA (pphm) | 10 | 10 | 10 | 10 | 10 | 10 | — |
| Texapon NSO initial charge/E feed (pphm) | 0.5/1 | 0.5/2 | 0.5/1 | 0.5/1 | 0.5/1 | 0.5/1 | 0.5/1 |
| NaPS in initial charge (pphm) | 0.19 | 0.19 | 0.19 | 0.19 | 0.19 | 0.19 | 0.19 |
| NaPS - feed (pphm) | — | — | — | — | — | — | — |
| NaPS addition (pphm) | — | 0.1 | — | 0.1 | 0.1 | 0.1 | 0.1 |
| Hydrogen peroxide addition (pphm) | 0.1 | — | 0.1 | — | — | — | — |
| Ascorbic acid (pphm) | 0.05 | 0.15 | 0.025 | 0.15 | 0.15 | 0.15 | 0.15 |
| Polymerization temp. (° C.) | 75 | 75 | 75 | 75 | 75 | 75 | 75 |
| Addition of the remaining monomer emulsion (min) | 5 | 5 | 5 | 5 | 60 | 60 | 60 |
| Swelling (min) | 60 | 60 | 60 | 60 | 60 | 60 | 60 |
| Part batch exit temp. (° C.) | 60 | 60 | 60 | 50 | 60 | 60 | 60 |
| Solids content (%) | 30.3 | 30.6 | 30.6 | 29.5 | 30.5 | 29.8 | 30.1 |
| Particle size (nm) | 55 | 67 | 62 | 66 | 77 | 74 | 66 |
| LT - 0.01% strength (%) | 98 | 98 | 98 | 97 | 98 | 96 | 97 |

TABLE 1d

Thickener dispersions according to the invention, redox/part-batch polymerized with swelling

| Thickener dispersion | Example 15 | Example 16 | Example 17 | Example 18 | Example 19 | Example 20 | Example 21 |
|---|---|---|---|---|---|---|---|
| n-Butyl acrylate (pphm) | — | 70 | 30 | 50 | 30 | 60 | 30 |
| Ethyl acrylate (pphm) | 70 | — | 20 | — | 30 | — | 20 |
| Methacrylic acid (pphm) | 30 | 30 | 40 | 40 | 40 | 40 | 30 |
| Acrylic acid (pphm) | — | — | — | — | — | — | 10 |
| PLEX 6877-O 25% strength in MMA (pphm) | — | — | 10 | 10 | — | — | 10 |
| Texapon NSO initial charge/E feed (pphm) | 0.5/1 | 0.5/1 | 0.5/1 | 0.5/1 | 0.5/1 | 0.5/1 | 0.5/1 |
| NaPS in initial charge (pphm) | 0.19 | 0.19 | 0.19 | 0.19 | 0.19 | 0.19 | 0.19 |
| NaPS - feed (pphm) | | | | | | | |
| NaPS addition (pphm) | 0.1 | 0.1 | 0.1 | 0.1 | 0.1 | 0.1 | 0.1 |
| Hydrogen peroxide addition (pphm) | — | — | — | — | — | — | — |
| Ascorbic acid (pphm) | 0.15 | 0.15 | 0.15 | 0.15 | 0.15 | 0.15 | 0.15 |
| Polymerization temp. (° C.) | 75 | 75 | 75 | 75 | 75 | 75 | 75 |
| Addition of the remaining monomer emulsion (min) | 60 | 60 | 60 | 60 | 60 | 60 | 60 |
| Swelling (min) | 60 | 60 | 60 | 60 | 60 | 60 | 60 |
| Part batch exit temp. (° C.) | 60 | 60 | 60 | 60 | 60 | 60 | 60 |
| Solids content (%) | 30.0 | 30.2 | 30.5 | 29.3 | 30.2 | 28.6 | 30.2 |
| Particle size (nm) | 73 | 64 | 74 | 75 | 72 | 64 | 87 |
| LT - 0.01% strength (%) | 97 | 98 | 96 | 96 | 97 | ? | ? |

Preparation of a Liquid Detergent

The following stock formulations were prepared (% by weight, based on the finished formulation):

|  | Formulation 1 | Formulation 2 |
|---|---|---|
| Lutensit ® A-LBS (99%; linear alkylsulfonate in acid form) | 17.92 | 13.44 |
| Lutensol ® AO 7 (nonionic surfactant) | 20 | 10 |
| Coconut fatty acid Edenor K8-18 | 8.5 | 8.5 |
| KOH | 5 | 4.38 |
| Sodium citrate dihydrate | 3 | 3 |
| 1,2-Propylene glycol | 8 | 8 |
| Ethanol | 2 | 2 |
| Water | qs | qs |

The above constituents were mixed and topped up to 90% by weight with water, i.e. a formulation gap of 10% by weight remained. The stock formulations were adjusted to pH 8.6 with KOH.

For the (unthickened) reference formulations, the stock formulations were topped up to 100% by weight with water. For the thickened test formulations, the stock formulations were topped up with thickener dispersion and water such that, taking into consideration the solids content of the dispersion, a thickener concentration of 1.5% by weight, based on the finished formulation, was established. Before the viscosity measurement, the formulations were left to rest for at least 5 hours.

Determination of the Low-Shear Viscosity

Taking into consideration the instructions in accordance with DIN 51550, DIN 53018, DIN 53019, viscosities of about 1000 mPas were measured using the Brookfield viscometer model RV-03 at a rotary speed of 20 revolutions per minute using spindle no. 62.

The transmission was measured in % at 440 nm at 23° C. The values found are given as a percentage, relative to the transmission of the unthickened reference formulation.

The results are summarized in Tables 2 and 3.

The invention claimed is:

1. A method of preparing an aqueous thickener dispersion from a monomer composition which comprises:
   a) at least one ethylenically unsaturated carboxylic acid,
   b) at least one ethylenically unsaturated hydrophobic monomer, and
   c) at least one ethylenically unsaturated associative monomer,
   where
   (i) an at least partially polymerized pre-emulsion is prepared from 10 to 80% by weight of the monomer composition and
   (ii) the remainder of the monomer composition is added in its entirety to the at least partially polymerized pre-emulsion and a free-radical polymerization is initiated with a redox initiator system.

2. The method according to claim 1, where the at least partially polymerized pre-emulsion of (i) is prepared in the presence of a thermally activatable initiator or a redox initiator.

3. The method according to claim 1, where the at least partially polymerized pre-emulsion of (i) is prepared by monomer feed procedure.

4. The method according to claim 3, where the at least partially pre-emulsion of (i) is prepared with a thermally activatable initiator or redox initiator and the thermally activatable initiator or redox initiator is essentially initially introduced in its entirety.

5. The method according to claim 1, where the free-radical polymerization of (ii) is initiated by adding a reducing agent component of a redox initiator system, where an oxidizing agent component of a redox initiator system has been added beforehand and/or excess initiator from (i) acts as an oxidizing agent component of a redox initiator system.

6. The method according to claim 1, where the free-radical polymerization of (ii) is initiated through essentially simultaneous addition of an oxidizing agent component of a redox initiator and of a reducing agent component of a redox initiator.

TABLE 2

Application-related assessment of the thickener dispersions: formulation 1 with 1.5% by weight of thickener

|  | C1 | C2 | C3 | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|---|---|---|
| Transmission in % | 79 | 92 | 98 | 99 | 100 | 100 | 100 | 100 | 100 | 99 | 100 | 99 | 99 |
| Viscosity (mPas) | 760 | 880 | 976 | 1280 | 1216 | 1216 | 1193 | 1200 | 1216 | 1312 | 1408 | 1504 | 1280 |

|  | Ex. 11 | Ex. 12 | Ex. 13 | Ex. 14 | Ex. 15 | Ex. 16 | Ex. 17 | Ex. 18 | Ex. 19 | Ex. 20 | Ex. 21 |
|---|---|---|---|---|---|---|---|---|---|---|---|
| Transmission in % | 99 | 78 | 99 | 87 | 75 | 97 | 96 | 98 | 94 | 92 | 96 |
| Viscosity (mPas) | 1520 | 896 | 1456 | 1216 | 996 | 1168 | 1488 | 1392 | 1584 | 1408 | 1344 |

TABLE 3

Application-related assessment of the thickener dispersions: formulation 2 with 1.5% by weight of thickener

|  | C1 | C2 | C3 | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|---|---|---|
| Transmission in % | 82 | 93 | 100 | 100 | 100 | 100 | 100 | 100 | 100 | 100 | 100 | 100 | 100 |
| Viscosity in mPas | 1100 | 1152 | 1456 | 1632 | 1808 | 1904 | 1888 | 1904 | 1904 | 2096 | 1960 | 2208 | 1632 |

|  | Ex. 11 | Ex. 12 | Ex. 13 | Ex. 14 | Ex. 15 | Ex. 16 | Ex. 17 | Ex. 18 | Ex. 19 | Ex. 20 | Ex. 21 |
|---|---|---|---|---|---|---|---|---|---|---|---|
| Transmission in % | 100 | 79 | 97 | 98 | 74 | 95 | 97 | 99 | 95 | 94 | 97 |
| Viscosity (mPas) | 2224 | 1232 | 2000 | 1792 | 1252 | 1584 | 1920 | 2032 | 1850 | 1990 | 2020 |

7. The method according to claim 1, where the at least partially polymerized pre-emulsion of (i) is left to swell in the presence of the remainder of the monomer composition for at least one hour before the free-radical polymerization is initiated.

8. The method according to claim 1, where the remainder of the monomer composition is added in (ii) to the at least partially polymerized pre-emulsion within a period of time of less than one hour after completion of (i) and, following complete addition, the free-radical polymerization is initiated immediately.

9. The method according to claim 1, where the at least one ethylenically unsaturated hydrophobic monomer is selected from C1-C9-alkyl(meth)acrylates, dienes, vinyl aromatics, (meth)acrylonitrile and mixtures thereof.

10. The method according to claim 1, where the at least one ethylenically unsaturated hydrophobic monomer comprises:
   b1) at least one $C_1$-$C_2$-alkyl methacrylate, and
   b2) at least one $C_2$-$C_9$-alkyl acrylate, where the alkyl chain length averaged over the number of alkyl groups of the alkyl acrylate is 2.1 to 4.0.

11. The method according to claim 1, where the at least one ethylenically unsaturated associative monomer is selected from $C_{10}$-$C_{30}$-alkyl(meth)acrylates and ethylenically unsaturated surfactant monomers.

12. The method according to claim 11, where the ethylenically unsaturated surfactant monomer has the general formula R—O—(CH$_2$—CHR'—O)$_n$—CO—CR"=CH$_2$ in which R is $C_6$-$C_{30}$-alkyl,
R' is hydrogen or methyl,
R" is hydrogen or methyl, and
n is a number from 2 to 100.

13. The method according to claim 1, where the monomer composition furthermore comprises an ethylenically polyunsaturated monomer.

14. The method according to claim 1, where the at least one ethylenically unsaturated carboxylic acid is selected from acrylic acid, methacrylic acid, itaconic acid and maleic acid.

15. The method according to claim 1, where the preparation of the at least partially polymerized pre-emulsion and/or the polymerization of the remainder of the monomer composition takes place in the presence of an anionic and/or nonionic emulsifier.

16. The method according to claim 15, in which the emulsifier has the general formula R—O—(CH$_2$—CHR'—O)$_n$—X in which R is $C_6$-$C_{30}$-alkyl,
R' is hydrogen or methyl,
X is hydrogen or SO$_3$M,
M is hydrogen or an alkali metal, and
n is a number from 2 to 100.

* * * * *